United States Patent [19]

Schulz et al.

[11] 4,302,539

[45] Nov. 24, 1981

[54] NOVEL SINGLE CELL PROTEIN SUBSTRATE

[75] Inventors: J. Gustav Schulz, Pittsburgh; Pamela M. Bunting, Cheswick, both of Pa.

[73] Assignee: Gulf Research & Development Company, Pittsburgh, Pa.

[21] Appl. No.: 164,392

[22] Filed: Jun. 30, 1980

Related U.S. Application Data

[63] Continuation-in-part of Ser. No. 77,247, Sep. 19, 1979, abandoned.

[51] Int. Cl.$^3$ .............................................. C12P 21/00
[52] U.S. Cl. ...................................... 435/68; 435/804; 435/243; 435/253; 435/255; 435/874; 435/921
[58] Field of Search ................. 435/68, 804, 253, 255, 435/243

[56] References Cited

U.S. PATENT DOCUMENTS

| | | | |
|---|---|---|---|
| 3,540,983 | 11/1970 | Rose et al. | 435/255 |
| 3,826,308 | 7/1974 | Compere-Whitney | 435/166 |
| 4,147,882 | 4/1979 | Schulz et al. | 562/410 |

Primary Examiner—Alvin E. Tanenholtz
Attorney, Agent, or Firm—Donald R. Cassady

[57] ABSTRACT

An acetone-insoluble organic acid product from the nitric oxidation of lignite is useful in growing single cell protein.

4 Claims, No Drawings

NOVEL SINGLE CELL PROTEIN SUBSTRATE

BACKGROUND OF THE INVENTION

This is a continuation-in-part to patent application Ser. No. 6/077,247 filed Sept. 19, 1979, titled "NOVEL SINGLE CELL PROTEIN SUBSTRATE" and now abandoned.

This invention relates to the growth of microorganisms as a protein source.

More particularly, this invention pertains to a valuable carbon source useful for the growth of such microorganisms.

Unicellular microorganisms, (single cell protein) commonly referred to as SCP, offer a potential of being a vast cheap course of food protein. For this reason much research effort has been devoted to finding and/or preparing inexpensive, non-toxic, and abundant nutrients for the growth of such organisms.

Early work included research on petroleum-based feedstocks, but the cost and availability of petroleum-derived carbon substrates made the economics of the process borderline. Little or no work is now being carried out on the production of SCP from petroleum-based feedstocks.

Limited work has been reported on the use of coal and coal-based chemicals as nutrients. In general, coal has been considered to be a poor substrate for microbial growth because microorganisms have not been shown to degrade or assimilate the bulk of the complex carbon-containing molecules in untreated coal at measurable rates and because coal contains microbially inhibitory phenolic compounds.

In 1966, Silverman et al., Nature Vol. 211, No. 5050, Aug. 13, 1966, published on the growth of *Candida lipolytica* on coal products. The paraffin-rich, hexane solubles fraction from Rockdale lignite low temperature tar supported growth of the yeast when phenolics had been removed. No growth of the yeast was obtained on coal acid mixtures or on an artificial mixture of polynuclear aromatic hydrocarbons found in high temperature coal tar.

In 1970, U.S. Pat. No. 3,540,983 reported the growth of Candida sp. on an aqueous extract of coal including lignite, but cell yields were low.

In 1974, U.S. Pat. No. 3,826,308 reported the fermentation-extraction of in situ fossil fuel deposits, such as coal or oil shale, with a plurality of microorganisms both sequentially and simultaneously, to produce valuable product and protein. The organisms comprise an anaerobic aromatic ring-reducing organism, a paraffin-oxidizing organism and an organic acid-modifying organism.

SUMMARY OF THE DISCLOSURE

We have found that an oxidation product of lignite is a useful carbon source in an aqueous mineral salts medium for the growth of microorganisms to manufacture protein.

The lignite oxidation product is the acetone insoluble, base soluble, solid fraction obtained from the low-temperature nitration and oxidation of lignite. The description of the lignite oxidation product and the method of manufacture thereof is fully described in U.S. Pat. No. 4,147,882, which patent disclosure is incorporated herewithin as fully and for all purposes as if it had herewithin been reproduced in full.

The microorganism is incubated in a sterile media containing the oxidation product of lignite as the sole source of carbon in the presence of a simple inorganic medium containing only the minerals necessary to sustain microbial growth.

DETAIL DESCRIPTION OF THE INVENTION

The oxidized lignite carbon source useful for this invention is prepared in the following manner:

The lignite, prior to use, is preferably ground in a suitable attrition machine, such as a hammermill, to a size such that at least about 50 percent of the lignite will pass through a 40-mesh (U.S. Series) sieve. The lignite is slurried in a suitable carrier, preferably water, prior to reaction with nitric acid. If desired, the lignite can be treated, prior to reaction herein, using any conventional means, to remove therefrom any materials forming a part thereof that will not be converted in reaction with nitric acid.

The reactant mixture is stirred while being maintained at a temperature of about 15° to about 200° C., preferably about 50° to about 100° C., and a pressure of about atmospheric to about 1000 pounds per square inch gauge (about atmospheric to about 70 kilograms per square centimeter), preferably about atmospheric to about 500 pounds per square inch gauge (about atmospheric to about 35 kilograms per square centimeter) for about two to about six hours. In order to obtain the desired mixture herein without losing appreciable amounts of carboxyl and/or nitro groups on the acids that are formed during the oxidation, and to obtain the desired acids in high yields it is absolutely critical that the reaction conditions therein, namely nitric acid concentration, temperature, pressure and reaction time, be so correlated to minimize and, preferably, to avoid decarboxylation and/or denitrofication.

The reaction product is removed from the reactor to a separator which can be, for example, a filter or a centrifuge.

The solids that are recovered in the separator are subjected to extraction with acetone. Such extraction can be carried out at a temperature of about 25° to about 150° C., and a pressure of about atmospheric to about 100 pounds per square inch gauge (about atmospheric to about seven kilograms per square centimeter). The solid material, insoluble in acetone, is removed.

The solid is soluble in base and can be neutralized to pH 7 without precipitation after dissolution in an aqueous media. A neutral aqueous solution of the acetone-insoluble material is then utilized as the carbon source for the growth of valuable aerobic and anaerobic microorganisms useful for their protein content.

Examples of representative genera of organisms which can be grown include the following aerobic and anaerobic organisms: Pseudomonas, Xanthomonas, Alcaligenes, Arthrobacter, Bacillus, Micrococcus, Azotobacter, Clostridium, Candida, Torulopsis, Rhodotorula, Debaryomyces, Endomycopsis, Hansenula, Penicillium, Aspergillus, Fusarium, and Geotrichum. This listing is not intended to be all-inclusive as a number of other microbial genera may also be cultivated on the coal acids.

In addition to required mineral nutrients, vitamins, amino acids, growth factors, and the like may be added to support or enhance growth. These components are well-known to those skilled in the art of growing single cell protein and are not considered to be unique or of novelty in the invention of this patent.

Harvesting of the protein is ideally accomplished by a mechanical separation as for example, centrifugation or filtration followed by sterilization and drying of solid protein.

EXAMPLE I

Several oxidation reactions were carried out on a North Dakota Lignite analyzing as follows, on a substantially moisture-free basis: 65.03 weight percent carbon, 4.0 weight percent hydrogen, 27.0 weight percent oxygen, 0.92 weight percent sulfur, 0.42 weight percent nitrogen, and 0.04 weight percent moisture. The ash was further analyzed and found to contain 43 weight percent oxygen, 7.8 weight percent sulfur, and the remainder metals. In each reaction, 100 milliliters of 70 percent aqueous nitric acid was gradually added to the stirred slurry containing 100 grams of powdered lignite defined above (corresponding to 67.5 grams of moisture-free feed) and 370 grams of water while maintaining the contents at between 70° to 150° C. and atmospheric pressure. Nitrogen oxides were permitted to escape from the reaction zone as they evolved.

At the end of the reaction period the product slurry was withdrawn from the reaction zone and filtered to obtain a solids fraction and a filtrate. For each reaction the solids were extracted with acetone at atmospheric pressure; the acetone-insoluble portions were dried at reduced pressure and combined to form a composite sample.

Bushnell-Haas mineral salts medium was prepared by dissolving the following inorganic salts in enough distilled water to make 1 liter of solution: $MgSO_4$, 0.2 g; $CaCl_2$, 0.02 g; $KH_2PO_4$, 1.0 g; $K_2HPO_4$, 1.0 g; $NH_4NO_3$, 1.0 g; and $FeCl_3$, 0.05 g. The solution was dispensed in 100 ml amounts into 250 ml Erlenmeyer flasks to which had been added either 3 g of the composite sample or 3 g of untreated lignite. The media were adjusted to pH 8 with NaOH, then sterilized by autoclaving at 120° C. for 20 minutes. The culture flasks were inoculated with 1.0 ml of a contaminated drilling mud which had been prepared from the composite sample. Immediately following inoculation, then again after 6 days' incubation on a rotary-action shaker at room temperature, aliquots were taken from each culture flask, serially diluted, and streaked to nutrient agar plates to determine the number of viable bacteria present. The results are shown in the following table:

| Carbon Substrate | Initial Bacterial Count (Colony Forming Units/ml) | Count Following 6 Days' Incubation (Colony Forming Units/ml) |
|---|---|---|
| 3% lignite | 5 million bacteria | 4 million bacteria |
| 3% composite | 5 million bacteria | 190 million bacteria |
| sample from $HNO_3$ oxidation | | |

EXAMPLE II

The predominant drilling mud contaminant, a bacterium having the characteristics of a pseudomanad, was isolated in pure culture. A small number of cells were picked from the surface of a nutrient agar slant of the bacterium and suspended in 10 ml of sterile distilled water taking care to avoid incorporation of any extraneous source of carbon. One ml of this inoculum suspension was added to a sterilized flask of medium consisting of 100 ml of Bushnell-Haas mineral salts medium and 1.0 g of the composite sample adjusted to pH 8. Bacterial growth was monitored and was found to increase from $2 \times 10^4$ microorganisms per ml initially to $4 \times 10^7$ microorganisms per ml in 3 days. After 7 days the count was $5.5 \times 10^7$ bacteria per ml. The culture was subcultured to identical medium with similar bacterial growth response.

EXAMPLE III

A distilled water suspension of a food quality yeast, *Candida tropicalis* ATTC 20326, was prepared by picking a small amount of yeast growth from a Sabouraud dextrose agar slant and suspending it in sterile distilled water. Bushness-Haas medium containing 1% of the composite sample was adjusted to pH 6.5 before autoclaving. The sterile medium was inoculated with 1 ml of the yeast cell suspension, then incubated on a rotary-action shaker at room temperature. Initially the culture contained $5 \times 10^2$ yeast cells per ml. After 3 days' and 7 days' incubation, yeast counts increased to $8 \times 10^3$/ml and $2 \times 10^5$/ml, respectively. Subsequent subculturing demonstrated more rapid yeast growth.

I claim:

1. In the process for manufacture of single cell protein comprising bacteria and fungus by growing a microorganism on fossil fuel carbon source the improvement which comprises using as the carbon source an oxidation-nitration product of lignite which is manufactured by subjecting a slurry of lignite in aqueous nitric acid to a temperature of from about 15° C. to about 200° C. for about 0.5 to about 15 hours, separating the solids, extracting the resulting solids with acetone, recovering the acetone-insoluble fraction, and dissolving the acetone-insoluble solid in base and neutralizing the solution to between pH 6.5 and pH 8.0.

2. The method of claim 1 wherein Pseudomonas single cell protein is manufactured.

3. The method of claim 1 wherein Candida single cell protein is manufactured.

4. The method of claim 3 wherein *Candida tropicalis* single cell protein is manufactured.

* * * * *